United States Patent
Fischer et al.

(10) Patent No.: US 9,645,376 B1
(45) Date of Patent: May 9, 2017

(54) SCANNER HEAD AND DEVICE WITH SCANNER HEAD

(71) Applicant: Abberior Instruments GmbH, Goettingen (DE)

(72) Inventors: Joachim Fischer, Karlsruhe (DE); Matthias Henrich, Heidelberg (DE); Gerald Donnert, Goettingen (DE); Matthias Reuss, Goettingen (DE)

(73) Assignee: ABBERIOR INSTRUMENTS GMBH, Goettingen (DE)

( * ) Notice: Subject to any disclaimer, the term of this patent is extended or adjusted under 35 U.S.C. 154(b) by 0 days.

(21) Appl. No.: 15/292,372

(22) Filed: Oct. 13, 2016

(30) Foreign Application Priority Data

Oct. 14, 2015 (EP) .................................... 15189728

(51) Int. Cl.
G02B 21/00 (2006.01)
G02B 21/26 (2006.01)
(Continued)

(52) U.S. Cl.
CPC ..... G02B 21/0048 (2013.01); G01N 21/6458 (2013.01); G02B 21/0032 (2013.01);
(Continued)

(58) Field of Classification Search
CPC ..... G01N 21/6458; G01N 2201/06113; G02B 21/0032; G02B 21/0048; G02B 21/0072;
(Continued)

(56) References Cited

U.S. PATENT DOCUMENTS 6,167,173 A 12/2000 Schoeppe et al.
6,486,458 B1 11/2002 Schoeppe et al.
(Continued)

FOREIGN PATENT DOCUMENTS

DE 197 02 753 A1 7/1998
DE 101 05 391 A1 8/2002
(Continued)

OTHER PUBLICATIONS

Stimulated Emission Depletion microscopy to study a myloid fibril formation (P. Mahou et al., Single Molecule Spectroscopy and Superresolution Imaging VIII, J. Enderlein et al. (ed.), Proc. of SPIE vol. 9331, 2015).
(Continued)

*Primary Examiner* — Mark R. Gaworecki
(74) *Attorney, Agent, or Firm* — Thomas | Horstemeyer, LLP (57) ABSTRACT

A scanner head for high-resolution scanning fluorescence microscopy comprises
  a first connector to connect the scanner head to a light microscope,
  second connectors to connect the scanner head to a light source and a fluorescence light detector,
  a beam shaper to shape a first part of the light from the light source into a first light intensity distribution in the focus of the light microscope comprising an intensity minimum surrounded by intensity maxima and a second part of the light into a second light intensity distribution in the focus of the light microscope comprising an intensity maximum at the location of the intensity minimum of the first light intensity distribution
  four tilting mirrors configured scan a sample with the light beam, and
  a deflector to deflect the fluorescence light to the second optical waveguide port.

20 Claims, 5 Drawing Sheets

(51) Int. Cl.
*G02B 21/36* (2006.01)
*G01N 21/64* (2006.01)

(52) U.S. Cl.
CPC ..... *G02B 21/0072* (2013.01); *G02B 21/0076* (2013.01); *G02B 21/26* (2013.01); *G02B 21/362* (2013.01); *G01N 2201/06113* (2013.01)

(58) Field of Classification Search
CPC ... G02B 21/0076; G02B 21/36; G02B 21/362
See application file for complete search history.

(56) References Cited

U.S. PATENT DOCUMENTS

| | | |
|---|---|---|
| 6,563,632 B1 | 5/2003 | Schoeppe et al. |
| 6,631,226 B1 | 10/2003 | Schoeppe et al. |
| 6,958,470 B2 | 10/2005 | Hoffmann |
| 8,520,280 B2 | 8/2013 | Engelhardt |
| 8,755,116 B2 | 6/2014 | Kastrup et al. |

FOREIGN PATENT DOCUMENTS

| | | |
|---|---|---|
| DE | 10 2007 025 688 A1 | 12/2008 |
| DE | 10 2014 113 716 A1 | 3/2016 |
| EP | 2 359 178 A1 | 8/2011 |
| WO | 90/00754 A1 | 1/1990 |
| WO | 2010/069987 A1 | 6/2010 |
| WO | 2010/133678 A1 | 11/2010 |

OTHER PUBLICATIONS

A STED Microscope Designed for Routine Biomedical Applications (F. Gërlitz et al., Progress in Electromagnetics Research, vol. 147, pp. 57-68, 2014).

European Search Report in co-pending related EP Application No. 16193665.3, mailed Jan. 4, 2017.

PicoQuant; MicroTime 200 STED, "Super-resolution add-on for the confocal time-resolved microscopy platform" Oct. 5, 2015 (Oct. 5, 2015), XP055329436, www.picoquant.com/images/uploads/downloads/microtime200__sted__brochure.pdf.

SCANNER HEAD AND DEVICE WITH SCANNER HEAD

CROSS REFERENCE TO RELATED APPLICATIONS

This application claims priority to co-pending European Patent Application No. EP 15 189 728.7 filed Oct. 14, 2015.

FIELD

The present disclosure relates to a scanner head for high-resolution scanning fluorescence microscopy. Furthermore, the present disclosure relates to a device for upgrading a light microscope to a high-resolution scanning fluorescence microscope comprising such a scanner head.

In the following, high-resolution scanning fluorescence microscopy is understood as scanning fluorescence microscopy, especially laser scanning microscopy, in which a sample is not only scanned with a focused light beam to excite it to emit fluorescence light, which is then registered and assigned to the respective position of the focused light beam in the sample, but in which a part of the focused light beam serves to narrow the spatial region from which the fluorescence light registered for the respective position of the focused light beam in the sample originates below the diffraction limit at the excitation wavelength. In order to do so, the light beam may—in addition to excitation light—comprise fluorescence inhibition light which, at the position of the intensity maximum of the excitation light, comprises an intensity minimum surrounded by intensity maxima and which inhibits the emission of fluorescence light everywhere outside of a small region around its intensity minimum. For example, the fluorescence inhibition light may be STED light, which impedes the emission of fluorescence light by excited fluorophores through stimulated emission. The fluorescence inhibition light may also be switching light which switches switchable fluorophores into a dark state not excitable to the emission of fluorescence by the excitation light.

BACKGROUND

A scanner head which is, however, not suitable for high-resolution scanning fluorescence microscopy is known from WO 90/00754 A1. The known scanner head comprises a lens which shapes excitation light emerging from a fiber optical waveguide into a parallel light beam. The light beam is deflected by two mirrors tiltable by drives and directed onto a sample via an ocular mount of a light microscope through the objective lens of the light microscope. For scanning the sample with the light beam focused by the objective lens, the mirrors are tilted. The fluorescence light emerging from the ocular in the opposite direction is directed back onto the lens by the mirrors and the lens injects the light into the fiber optical waveguide. The fiber optical waveguide branches off in the direction of a light source for providing the excitation light one the one hand and to a detector for registering the fluorescence light on the other hand. The light source and the detector therefore are not part of the scanner head but are connected to the latter through the fiber optical waveguide. A control for the drives of the mirrors is also provided outside of the scanner head.

A laser scanning microscope in known from DE 197 02 753 A1, corresponding to U.S. Pat. No. 6,167,173 A and U.S. Pat. No. 6,486,458 B1, which comprises an arrangement for injecting laser radiation into a scanner head with a scanner deflecting at least in two dimensions. The radiation is focused into a sample through a light microscope. The injection of the radiation is achieved through at least one fiber optical waveguide, while collimation optics for collimation of the divergently emerging radiation is provided downstream of the fiber end at the scanner head. Seen from the direction of the sample, downstream of the scanner in the scanner head a detector for detecting the radiation from the scanned object is provided.

A high-resolution scanning fluorescence microscope and a module for a high-resolution scanning fluorescence microscope are known from DE 101 05 391 A1, corresponding to U.S. Pat. No. 6,958,470 B2. The high-resolution scanning fluorescence microscope comprises a light source for emitting an excitation light beam suitable for exciting an energy state of the sample, a detector for detecting emission light and a stimulating light beam coming from the light source for causing stimulated emission in the sample excited by the excitation light beam. The excitation light beam and the stimulating light beam are arranged in such a way that their intensity distributions partly overlap in a focal region. Optical elements shaping the stimulating light beam are combined into at least one module which may be positioned in the beam path of the scanning fluorescence microscope. In practical terms, the module may have a bayonet mount with which it is connectable to a corresponding mount of the scanning fluorescence microscope. With the known module for a high-resolution scanning fluorescence microscope, existing scanning fluorescence microscopes are intended to be upgraded to STED microscopes. The adjustment of the optical elements shaping the stimulating light beam with respect to the scanning fluorescence microscope to reach a full function of the scanning fluorescence microscope as an STED microscope, however, proves to be difficult. The stimulating light beam only then has its intended intensity distribution in the focal region if it is aligned exactly with respect to a pupil of the objective lens of the scanning fluorescence microscope and if it keeps this alignment when scanning the sample with the scanner of the scanning fluorescence microscope.

Under the heading of "easySTED", high-resolution scanning fluorescence microscopes are known in which the excitation light and the fluorescence inhibition light together pass through beam-shaping optics which, however, has a different effect on the excitation light and the fluorescence inhibition light. Especially, the fluorescence inhibition light is shaped in such a way that it comprises an intensity minimum surrounded by intensity maxima at the intensity maximum of the excitation light focused in a diffraction-limited spot. Examples for beam-shaping optics which come under the heading of "easySTED" are described in DE 10 2007 025 688 A1, corresponding to U.S. Pat. No. 8,755,116 B2, WO 2010/133678 A1 and DE 10 2014 113 716 A1.

From EP 2 359 178 A1, corresponding to U.S. Pat. No. 8,520,280 B2, a device for dynamic shift of a light beam with respect to optics focusing the light beam and comprising a pupil is known. The dynamic shift is accomplished in order to scan an object in a two-dimensional scanning area with the focused light beam. The device has beam deflectors, which deflect the light beam in two different directions with respect to the optical axis of the optics by dynamically adjustable deflection angles. For each direction at least two beam deflectors are series-connected and may be controlled independently of each other so that the beam position of the light beam in the respective direction within the pupil of the focusing optics as well as the angle of the light beam with respect to the optical axis of the focusing optics and therefore the position of the focused light beam in the sample region may be set. In this way it becomes possible to scan the two-dimensional scanning region without variation of the optical conditions above the scanning region. In this way it is e. g. prevented that the spatial phase structure of the stimulating beam shifts within the pupil during STED microscopy. Such shifts lead to the desired light intensity distribution of the focused stimulating beam not having the low intensity minimum surrounded by high intensity maxima at the location of the intensity maximum of the excitation light beam. Furthermore, with the known device distances of the deflectors to the pupil or of a pupil image of the focusing optics as well as lens aberrations of the focusing objects and aberrations of the beam deflectors may be compensated. Furthermore, the pivoting point of the deflected light beam may be set in an axial direction in order to e.g. provide for different axial positions of different objective lenses.

The scientific publication "*Stimulated Emission Depletion microscopy to study a myloid fibril formation*" (P. Mahou et al., Single Molecule Spectroscopy and Superresolution Imaging VIII, J. Enderlein et al. (ed.), Proc. of SPIE Vol. 9331, 2015) discloses a "home-built" STED microscope using a light microscope and an optical setup external to the light microscope. The optical setup includes a laser light source emitting a light beam. The light beam is split into an excitation beam and a depletion beam. The excitation beam is fed through a light path including 30 m (98 ft) of optical fiber. The depletion beam is fed through a separate light path including 100 m (328 ft) of optical fiber, in the course of which it is shaped into a "doughnut" shape, so as to provide stimulated emission depletion to prevent fluorescence emission. Through a first dichroitic mirror, both light beams are employed to scan a sample using an objective lens of the light microscope and a quad scanner comprising four tilting mirrors. The fluorescence light from the sample is fed back through the light microscope objective lens, the quad scanner and the first dichroic mirror before being deflected onto a detector by a second dichroic mirror.

There still is a need of a scanner head by which existing light microscopes of different types and different manufacturers can be upgraded to high-resolution scanning fluorescence microscopes without problems.

SUMMARY

The invention provides a scanner head for high-resolution scanning fluorescence microscopy. The scanner comprises a housing, a first connector arranged on or in the housing and configured to connect the scanner head to a light microscope, and second connectors arranged on or in the housing and configured to connect the scanner head to an external light source and an external fluorescence light detector via fiber optical waveguides. A beam shaper is encased in the housing and arranged between the second connectors and the first connector and configured to shape light from the external light source into a light beam. Furthermore, tilting mirrors are encased in the housing and arranged between the beam shaper and the first connector and configured to deflect the light beam by different deflection angles in such a way that a sample into which the light beam is focused by the light microscope is scanned in two different directions by the light beam, while fluorescence light from the sample is guided back to the second connectors.

The first connector is configured to connect the scanner head to a mount of the light microscope. The mount has a first defined relative position with regard to an intermediate image of the sample imaged by the light microscope so that the intermediate image has a second defined relative position with regard to the tilting mirrors. The second connectors comprise a first optical waveguide port configured to receive the light from the light source and a separate second optical waveguide port configured to output the fluorescence light to the detector.

A deflector is arranged between the tilting mirrors and the first optical waveguide port and configured to deflect the fluorescence light to the second optical waveguide port. The beam shaper is configured to shape a first part of the light from the light source into a first light intensity distribution in the focus of the light microscope comprising an intensity minimum surrounded by intensity maxima and a second part of the light from the light source into a second light intensity distribution in the focus of the light microscope comprising an intensity maximum at the location of the intensity minimum of the first light intensity distribution. The tilting mirrors include four tilting mirrors each having a drive and a tilting axis. The four drives are configured to be controlled independently of each other in order to tilt the four tilting mirrors around their respective tilting axes.

The invention also provides a device for upgrading a light microscope to a high-resolution scanning fluorescence microscope. The device comprises a scanner head according to the invention, and a base unit comprising a light source providing the light, a detector configured to detect fluorescence light and a controller configured to control the drives of the tilting mirrors. The device furthermore comprises a first optical waveguide leading from the light source to the first optical waveguide port of the scanner head, a second optical waveguide leading from the second optical waveguide port to the detector and a control cable leading from the controller to the drives of the tilting mirrors.

The invention also provides a high-resolution scanning fluorescence microscope comprising a light microscope comprising a mount having a first defined relative position with regard to an intermediate image of a sample imaged by the light microscope, a light source providing light, a fluorescence light detector configured to detect fluorescence light, a first optical waveguide, a first end of the first optical waveguide being connected to the light source, a second optical waveguide, a first end of the second optical waveguide being connected to the detector, a controller, a control cable, a first end of the control cable being connected to the controller, and a scanner head according to the invention, the scanner head being connected to the second ends of the first and the second optical waveguides and of the control cable.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

A scanner head for high-resolution scanning fluorescence microscopy according to the present disclosure comprises a housing. A first connector is arranged on or in the housing and configured to connect the scanner head to a mount of a light microscope, which has a first defined relative position with regard to an intermediate image of the sample imaged by the light microscope. This means especially that the first connector is configured for connecting the scanner head to a camera mount or to another fully corrected and/or standardized or normed mount with a defined relative position of an intermediate image of the light microscope in order to, for example, be able to record an image of the individual sample viewed with the light microscope with a camera. Such a camera mount is present in many light microscopes of different types and different manufacturers. It aligns a mounted camera in a defined way with respect to an image plane of the light microscope. In practical terms, the mount with the first defined relative position of an intermediate image of the light microscope may be a so-called C mount, which has a mounting thread with a stop in a defined distance to an image plane of the light microscope. Many existing light microscopes have a C mount.

In addition to the first connector for connecting to the mount, the scanner head according to the present disclosure has second connectors arranged on or in the housing, which are configured for connecting the scanner head to an external light source via the fiber optical waveguides and to an external detector for fluorescence light, and which include separate optical waveguide ports for the light from the light source and the fluorescence light to the detector. That is, the second connectors comprise a first optical waveguide port configured to receive the light from the light source and a separate second optical waveguide port configured to output the fluorescence light to the detector. These separate waveguide ports are prerequisite for the light from the external light source and the fluorescence light to the external detector each being guided via ideally adapted fiber optical waveguides. This is necessary due to the fact that for the light from the light source in high-resolution scanning fluorescence microscopy a polarization-preserving single-mode fiber optical waveguide is required, as a rule, while for the fluorescence light a multi-mode fiber optical waveguide is to be used to avoid intensity losses.

A beam shaper of the scanner head according to the present disclosure is encased in the housing and arranged between the second connectors and the first connector and configured to shape light from the external light source into a light beam. The beam shaper is configured to shape a first part of the light from the light source into a first light intensity distribution in the focus of the light microscope comprising an intensity minimum surrounded by intensity maxima, and to shape a second part of the light from the light source into a second light intensity distribution in the focus of the light microscope comprising an intensity maximum at the location of the intensity minimum of the first light intensity distribution. The first part of the light from the light source is especially designed to be stimulation light while the other part of the light from the light source is especially designed to be excitation light. The elements of the beam shaper which shape the two parts of the light from the light source in different ways may be arranged separate from each other so that either just the first or just the second part of the light from the light source is transmitted through them. In this case, the two parts of the light from the light source are subsequently joined, and when they enter the beam shaper together they are separated when entering the beam shaper. Suitable beam shapers are known to the person skilled in the art in the field of STED microscopy.

Furthermore, the scanner head according to the present disclosure comprises tilting mirrors which are encased in the housing and arranged between the beam shaper and the first connector, and which are configured to deflect the light beam by different deflection angles in such a way that a sample into which the light beam is focused by the light microscope is scanned in two different directions by the light beam, while fluorescence light from the sample is guided back to the second connectors. This means that the mount not only has the first defined relative position with regard to an intermediate image of the sample imaged by the light microscope, but the intermediate image also has a second defined relative position with regard to the tilting mirrors.

Four tilting mirrors with a drive each are present, corresponding to two tilting mirrors per direction in which the sample is scanned. The drives of the tilting mirrors may be controlled independently of each other to tilt the four tilting mirrors around their respective tilting axes. The tilting mirrors constitute the scanner of the scanner head according to the present disclosure. Their function, however, is not limited to that of a scanner. By the four tilting mirrors, the light beam may be deflected in such a way that it passes through the pupil of the objective lens of the respective light microscope not only under a desired angle but also at a desired position. This is especially a prerequisite for the first part of the light focused by the light microscope to indeed realize the intensity minimum surrounded by the intensity maximum. With the aid of the tilting mirrors, axial offsets between the axis of the mount and the center of the pupil of the objective lens of the light microscope may be compensated as well as all other optical and alignment errors which are already mentioned in EP 2 359 178 A, see above, as being compensable by means of such an arrangement of tilting mirrors.

Furthermore, the scanner head according to the present disclosure has a deflector which is arranged between the tilting mirrors and the first optical waveguide port and configured to deflect the fluorescence light to the second optical waveguide port. In this way, the fluorescence light de-scanned by the tilting mirrors is separated from the beam path of the light from the light source and led towards the separate second optical waveguide port provided for the fluorescence light. The separation may be upstream or downstream with respect to the beam shaper as seen from the direction of the tilting mirrors, where a separation after the beam shaper only is expedient when the beam shaper completely passes on the fluorescence light, i.e. no major intensity losses are incurred when the fluorescence light passes through the beam shaper.

All features of the scanner head according to the present disclosure described up to here are essential for the scanner head being compatible to different light microscopes, i.e. light microscopes of different types and/or different manufacturers, so that scanner head and light microscope be combined into a high-resolution scanning fluorescence microscope. That in this way existing light microscopes of different types and different manufacturers can be upgraded to high-resolution scanning fluorescence microscopes without problems is surprising in view of the fact that scanner heads to upgrade different light microscopes to scanning fluorescence microscopes are not widely distributed due to the adjustment effort incurred. Generally, the adjustment effort in a high-resolution scanning fluorescence microscope is even higher. In the scanner head according to the present disclosure, this problem is managed by means of the four tilting mirrors.

The housing of the scanner head is a single housing, on or in which the first connector and the second connector are provided and which surrounds all other parts of the scanner head. The housing may substantially be provided as an encasing of the optical setup of the scanner head, which may have its own supporting structure. Alternatively, the housing or parts of the housing may also form a structure supporting the optical setup of the scanner head.

The present disclosure takes a fundamentally different path from DE 101 05 391 A1, which teaches a module for the shaping of the stimulating light beam to upgrade an existing scanning fluorescence light microscope to an STED microscope using the scanner of the existing scanning fluorescence microscope. On the contrary, the scanner head according to the present disclosure has its own and very special scanner. In this way, it is not only possible to upgrade ordinary light microscopes into high-resolution scanning fluorescence microscopes but due to the special formation of the scanner, the adaptation of the scanner head to the individual light microscope may be done by its scanner, i.e. with the help of its tilting mirrors.

If a scanner head according to the present disclosure is combined with an existing scanning fluorescence microscope, this has to be done outside the actual scanning fluorescence microscope, i.e. in such a way that the scanner head is not placed in the beam path of the scanning microscope but in the beam path of the light microscope included in the scanning microscope. This means especially that between the objective lens of the light microscope used and the scanner head according to the present disclosure no scanner constituting the scanning fluorescence microscope may be placed, and that only the scanner of the scanner head lies in the beam path to and from the sample.

By going without a scanner possibly already present and providing its own, comparatively complex, scanner in the scanner head according to the present disclosure, the desired adaptation of the scanner head according to the present disclosure to different existing light microscopes is enabled. The further features of the scanner head according to the present disclosure make sure that with its help high-resolution scanning fluorescence microscopy may be carried out and that all the parts directly relevant for alignment of the optical setup are part of the mechanically continuous scanner head while all other parts are placed outside the scanner head. In this way not only the light source but also the detector is moved out of the scanner head and connected via a fiber optical waveguide.

The mount of the light microscope to which the scanner head may be connected may be a camera mount or another fully corrected and/or standardized mount of the light microscope.

In this way it is made possible for the first connector to be configured for fixed-location support of the scanner head on the mount. This means that the scanner head according to the disclosure, especially if connected to a vertically oriented mount, may lack additional supports except for those on the mount. The scanner head according to the present disclosure does not put more mechanical strain on the mount than a larger camera for which the mount is usually intended.

The tilting mirrors of the scanner of the scanner head according to the present disclosure may be arranged around a plane onto which an intermediate image of the light microscope falls due to the standardization of the mount. The defined position of the intermediate image with respect to the mount of the light microscope is exploited in the scanner head according to the present disclosure to arrange the tilting mirrors of the scanner around this image plane. However, no very particular placement of the tilting mirrors with respect to this image plane is necessary, because with the four independent tilting mirrors any divergences of the orientations of the individual tilting mirrors may be compensated.

Usually, the tilting mirrors of the scanner of the scanner head according to the present disclosure are the only movable parts of the scanner head. The waste heat occurring due to their controlled movement may, together with heat occurring in the scanner head due to light unintentionally converted into heat, usually be vented into the surroundings of the scanner head without special cooling devices by convection only (if necessary enhanced by cooling elements). Especially, no movable cooling devices are necessary, which could induce any vibrations of the scanner head. The drives of the tilting mirrors may be realized in such a way that their use causes no undesired vibrations of the scanner head.

Preferably, in the scanner head according to the present disclosure the first and second optical waveguide ports are parallel to each other and placed on a side of the scanner head opposite to the first connector. The scanner head therefore has an axial setup substantially along an optical axis defined by the mount of the light microscope, and therefore the scanner head, due to its compact dimensions, is well balanced orthogonally to the optical axis with respect to the mount when the mount is vertically oriented.

In a preferred embodiment of the scanner head according to the present disclosure, the beam shaper comprises beam shaping optics through which the first and second parts of the light from the light source pass on a common light path and which shapes the first part of the light in such a way that it comprises the intensity minimum surrounded by the intensity maxima in the focus of the light microscope, whereas it shapes the second part of the light in such a way that it comprises the intensity maximum at the place of the intensity minimum of the first part of the light in the focus of the light microscope. This means that the beam shaper implements the so-called easySTED concept, as it is as such described in DE 10 2007 025 688 A1, corresponding to U.S. Pat. No. 8,755,116 B2, WO 2010/133678 A1 and DE 10 2014 113 716 A1, and the actual easySTED embodiments disclosed here may also be realized in the scanner head according to the present disclosure. Due to easySTED beam shaping optics, the scanner head according to the present disclosure is especially compact because no separated light path for the first and the second part of the light from the light source is present and therefore no light paths have to be separated and joined again.

Especially, the beam shaper may conform to one of the embodiments of the device for separate modulation of wavefronts of two components of the light beam described in DE 10 2014 113 716 A1, which comprise a spatial light modulator and in which the two components correspond to the first part of the light from the light source of the present disclosure, while a further component of a different wavelength also passing through the earlier-described device, but not modulated, corresponds to the second part of the light from the light source of the present disclosure. Especially, the beam shaper may have the optical setup shown in FIG. 1 of DE 10 2014 113 716 A1. In all embodiments of the device according to DE 10 2014 113 716 A1, the intensity distribution of the first part of the light from the light source serving as fluorescence inhibition light may, especially by control of the spatial light modulator, be adjusted in such a way that its intensity minimum in the focus of the light microscope is limited by its intensity maxima in all three spatial dimensions, i.e. also in the z direction of an optical axis of the objective lens of the light microscope.

In practical terms, maximum dimensions of the scanner head according to the present disclosure, both in the direction of the optical axis and perpendicular to it, may be 25 cm (9.8 in) or less. In practical terms, the scanner head including a rectangular housing in the direction of the optical axis may be 2 dm (8 in) high and 1 to 1½ dm (4 to 6 in) wide or deep. The mass of the scanner head may be 2 kg (4.4 lb) at maximum, preferably 1.5 kg (3.3 lb) at maximum or even more preferably 1.2 kg (2.6 lb) at maximum. Often it is about 1 kg (2.2 lb).

Because for the light from the light source preferably a polarization-preserving single-mode fiber optical waveguide is used while for the fluorescence light to the detector preferably a multi-mode fiber optical waveguide is used, the first optical waveguide port may especially be configured for connecting a single-mode fiber optical waveguide and the second optical waveguide port may especially be configured for connecting at least one multi-mode fiber optical waveguide. The fiber optical waveguides may be separable independently of each other or fixedly connected to the optical waveguide ports. Fixedly connected fiber optical waveguides may be considered as part of the scanner head.

Furthermore, the scanner head according to the present disclosure may comprise a control cable port for a control cable for connecting the drives of the tilting mirrors to an external controller. The control cable port may be provided directly at the drives or on the housing of the scanner head. The control cable may be detachable or fixedly connected to the control cable port. A fixed control cable may be considered as part of the scanner head. Preferably, only the drives are located in housing of the scanner head. Generally, driver units of the drives, which are to be placed as close as possible to the drives, may also be part of the scanner head. Preferably, however, such driver units are also provided externally and connected to the scanner head via the control cable.

A device for upgrading a light microscope to a high-resolution scanning fluorescence microscope according to the present disclosure, apart from a scanner head according to the present disclosure, comprises a base unit which comprises a light source providing the light, a detector for the fluorescence light and a controller for controlling the drives of the tilting mirrors. From the light source a first optical waveguide leads to the first optical waveguide port of the scanner head. A second optical waveguide leads from the second optical waveguide port to the detector. Additionally, a control cable leads from the controller to the drives of the tilting mirrors of the scanner head.

As repeatedly mentioned before, the first optical waveguide preferably comprises a polarization-preserving single-mode fiber optical waveguide, while the second optical waveguide preferably comprises a multi-mode optical waveguide.

The base unit may comprise a supply port for supplying a supply low voltage. The supply low voltage may be provided with a customary mains adapter. In this way, especially an adaptation of the base unit to different public power grids may be achieved by choosing the individual matching mains adapter.

Furthermore, the base unit may have a communication port for connecting to a control computer. Through this communication port, which may correspond to a usual standard such as for example USB, the base unit and, through the base unit, the scanner head may be controlled by the control computer. In order to do this, special software may be provided for installation on the control computer.

The light source placed in the base unit may essentially consist of at least two lasers which emit at different wavelengths. In STED microscopy, it makes sense for these different wavelengths to be wavelengths which are especially suited for excitation light on the one hand and stimulating light on the other hand. Especially pulsed lasers but also CW lasers may be used as lasers. Especially, inexpensive laser diodes may be employed.

To enable three-dimensional scanning of a sample with the light from the light source focused by the light microscope in the device according to the present disclosure, a sample holder height-adjustable by controlling an actuator may be provided. The actuator may be connected to a further controller in the base unit by a further control cable. This sample holder replaces or supplements the sample holder of the light microscope and serves to shift the sample in z direction, i.e. in the direction of an optical axis of the objective lens of the light microscope with respect to the intensity minimum surrounded by intensity maxima of the first part of the light serving as fluorescence inhibition light. It only makes sense to use such a height-adjustable sample holder in combination with a beam shaper of the scanner head, which shapes the first part of the light serving as fluorescence inhibition light in such a way that its intensity minimum in the focus of the light microscope is also surrounded by its intensity maxima in the z direction. Such beam shapers are e.g. described in DE 10 2014 113 716 A1.

Figure 1:
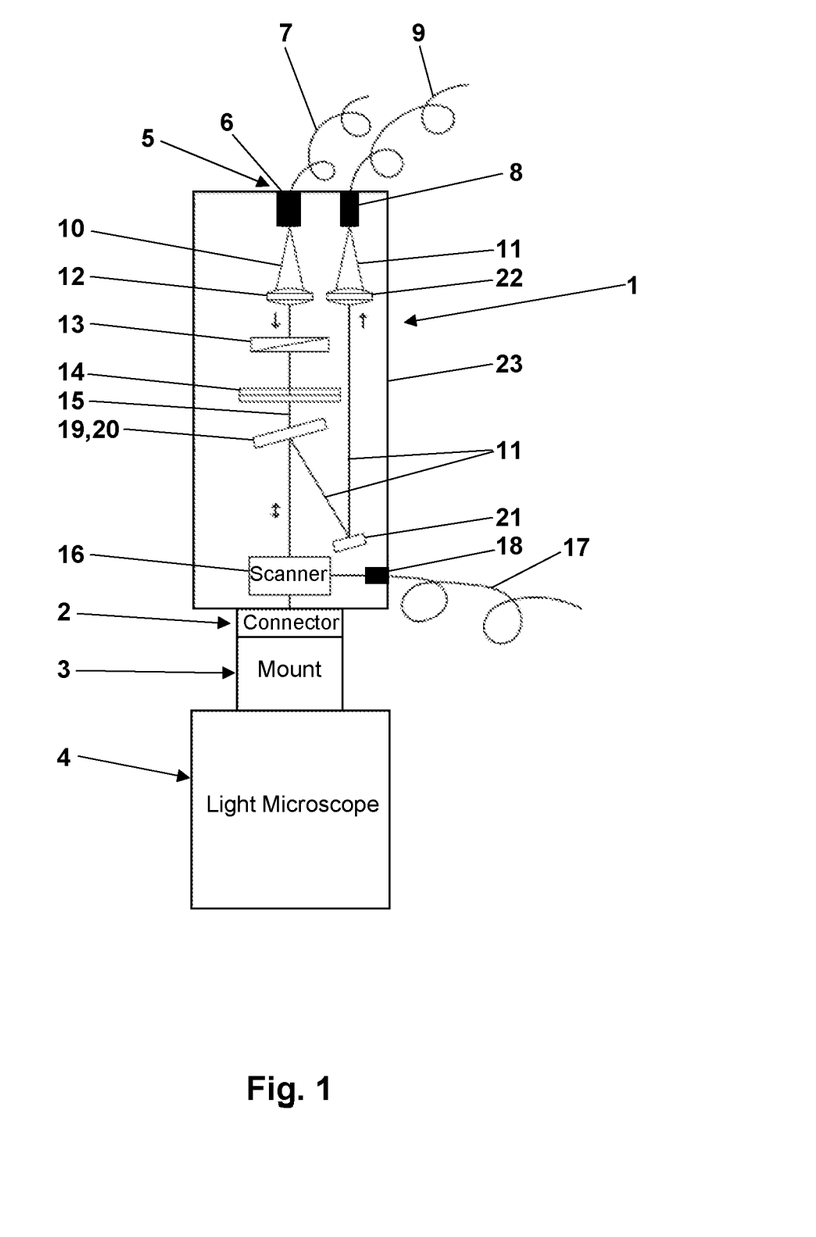
FIG. 1 schematically shows a scanner head according to the present disclosure connected to a light microscope.

Now referring in greater detail to the drawings, the scanner head 1 schematically shown in FIG. 1 is connected to a fully-corrected mount 3 of a light microscope 4 via a first connector 2, in respect to which a first relative position of an intermediate image of the light microscope 4 is defined. For example, the mount 3 may be a camera mount and especially a so-called C mount. Two second connectors 5 of the scanner head 1 comprise a first optical waveguide port 6 for connecting a polarization-preserving single-mode first fiber optical waveguide 7 and a second optical waveguide port 8 for connecting a multi-mode second fiber optical waveguide 9. Through the first fiber optical waveguide 7, the scanner head 1 is provided with light 10 from an external light source not shown here. Through the second fiber optical waveguide 9, fluorescence light 11 from the scanner head is guided to an external detector for registering the fluorescence light 11 also not shown here. The light 10 emerging from the first fiber optical waveguide 7 is shaped in such a way by beam shapers 12 to 14, which are placed between the second connectors 5 and the first connector 2, that a first part of the light 10, which serves as fluorescence inhibition light and which may be a light that causes excited fluorophores to have stimulated emission, comprises an intensity minimum surrounded by intensity maxima in the focus of the light microscope 4. On the contrary, a second part of the light 10, which serves as excitation light for exciting the fluorophores into emission of fluorescence light has an intensity maximum at the location of the intensity minimum of the fluorescence inhibition light in the focus of the light microscope 4. Both parts of the light 10 pass through the beam shapers 12 to 14 together, which, however, at least partly act wavelength-dependently on the two parts of the light comprising different wavelengths. As a first step, the light 10 is collimated with a coupling lens 12. Then the linearly polarized light 10 is circularly polarized with a quarter-wave plate ($\lambda/4$ plate) 13. Subsequently, the circularly polarized light 10 passes through a phase plate 14. The phase plate 14 is the actual achromatic element of the beam shapers 12 to 14 and causes the different shaping of the two parts of the light 10 with respect to their light intensity distributions in the focus of the light microscope 4. The light beam 15, into which the light 10 is shaped in this way, is dynamically deflected by a scanner 16, to scan a sample with the superimposed light intensity distributions of the two parts of the light 10. The scanner 16 is especially realized according to WO 2010/069987 A and comprises at least four tilting mirrors with independently controllable drives. The scanner 16 therefore is not only suitable for scanning the sample in the light microscope 4 as desired, but also for compensating all misalignments between the scanner head 1 and the light microscope 4. In this way, the scanner head 1 may be used with different light microscopes 4 without constructive changes on the scanner head 1 having to be made. The scanner 16, i.e. the drives of its tilting mirrors, is controlled by an external controller not shown here. In order to do this, the scanner 16 is connected to the external controller by a control cable 17, for which a control cable port 18 is provided on the scanner head 1. The fluorescence light 11 emitted by the individual sample and emitted from the light microscope 4 is separated from the beam path of the light 10, i.e. the light beam 15, with the help of a dichroic mirror 19 as a deflector 20, and aligned in parallel to the light beam 15 with a full mirror 21. Afterwards, the fluorescence light 11 is injected into the multi-mode second fiber optical waveguide 9 by a further coupling lens 22. As the deflector 20 is placed behind the scanner 16 as seen from the light microscope 4, the scanner 16 de-scans the fluorescence light 11 which therefore, behind the scanner 16, always has a uniform direction in which it enters the multi-mode fiber optical waveguide 9. Due to the parallel orientation of the fluorescence light 11 to the light beam 15, the optical waveguide ports 6 and 8 are placed next to each other on the side of the scanner head 1 facing away from the first connector 2. The first connector 2 and the second connectors 5 as well as the control cable port 18 are placed on and all further components of the scanner head 1 are placed in a housing 23 of the scanner head 1, to which a possible supplemental support structure of these further components is fixed—or conversely the housing is fixed to this support structure. The entire scanner head 1 has a typical length in the direction of the optical axis of the mount 3 of 2 dm (8 in) and a maximum diameter orthogonally to the optical axis of 1½ dm (6 in). Its typical weight is 2 kg (4.4 lb). When the optical axis is vertically oriented, the scanner head 1 typically is only supported on the mount 3 and not additionally supported.

Figure 2:
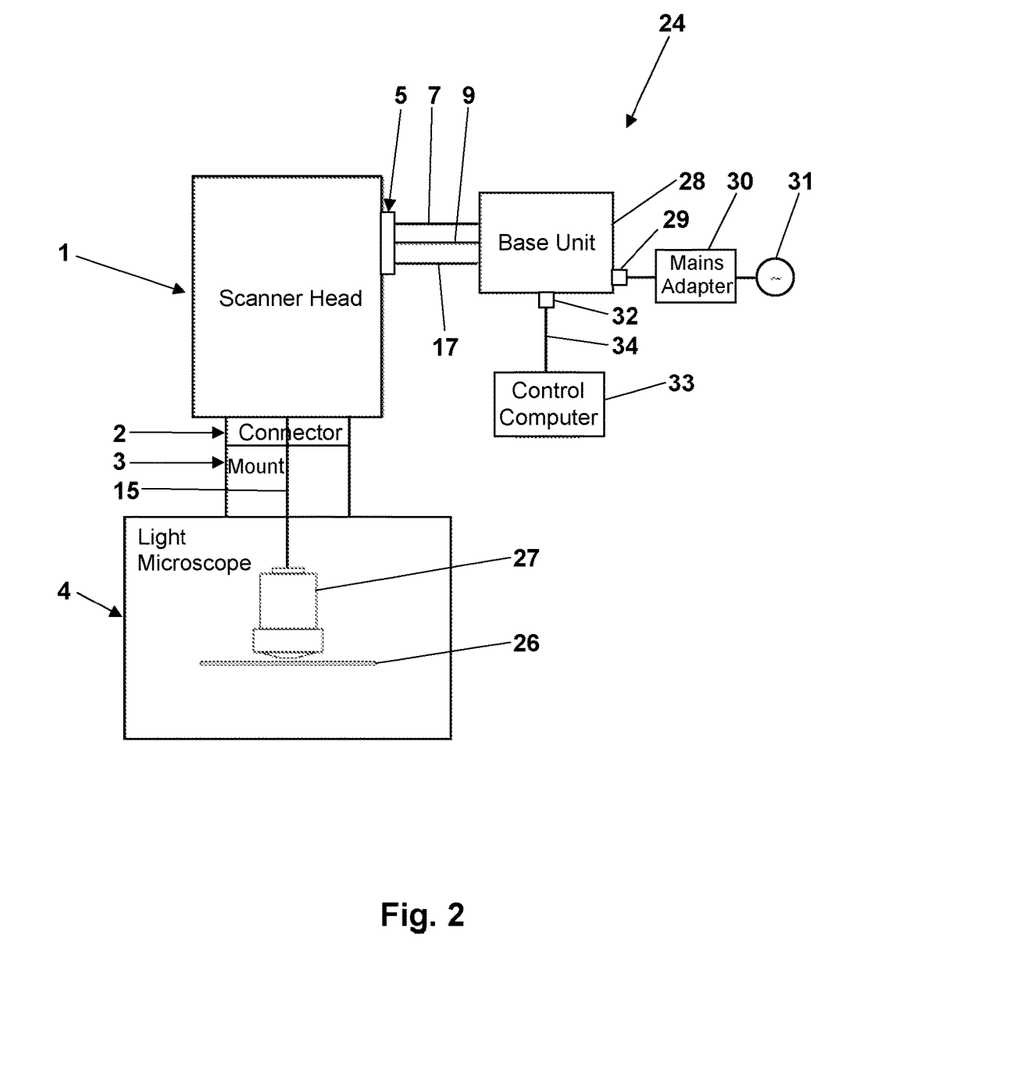
FIG. 2 schematically shows a device according to the present disclosure with a scanner head according to the present disclosure connected to a light microscope.

FIG. 2 shows an embodiment of the scanner head 1 modified with respect to FIG. 1 as part of a device 24 by means of which the light microscope is upgraded into a high-resolution scanning fluorescence microscope 25. A sample 26 to be examined and an objective lens 27 of the light microscope 4 with which the light beam 15 is focused into the sample 26 are schematically shown in the light microscope 4. The scanner head 1 is provided for scanning the sample 26 with the focused light beam 15 and for shaping the light into the light beam 15 with the desired light intensity distributions in the focus of the objective lens 27. The scanner head 1 exclusively uses the objective lens 27 of the light microscope 4 and the holder for the sample 26. The device 24 does not use a possible own scanner of the light microscope 4; the scanner head 1 does not lie in the scanned beam path of such an own scanner of the light microscope 4. Here, the second connectors 5 of the scanner head 1 are also provided for connecting the control cable 17. The control cable 17, like the single-mode first fiber optical waveguide 7 and the multi-mode second fiber optical waveguide 9, leads to a base unit 28 in which the light source, which feeds the light 10 into the single-mode first fiber optical waveguide 7 according to FIG. 1, the detector, which detects the fluorescence light 11 injected into the multi-mode second fiber optical waveguide 9 according to FIG. 1, and the external controller, which controls the drives of the tilting mirrors of the scanner 16 according to FIG. 1, are placed. The base unit 28 is supplied with a supply low voltage by a mains adapter 30 via a supply port 29. The mains adapter 30 is supplied by an AC grid 31 of local standards, to which only the mains adapter 30 is adapted. Furthermore, the mains adapter 30 is adapted to the power requirement of the base unit 28; apart from that it is an unspecific standard component. The base unit 28 furthermore comprises a communication port 32 for connecting a control computer 33 via a communication cable 34, for example according to the USB standard. The light source, which is a part of the base unit 28, comprises at least two lasers which emit light at different wavelengths, and the light of which is joined together to form the light 10, which is supplied to the scanner head 1 via the single-mode first fiber optical waveguide 7 according to FIG. 1. The detector generally may comprise several detector units selectively sensitive for different wavelengths of the fluorescence light 11 according to FIG. 1, or it may be tunable to a certain wavelength of the fluorescence light 11 by means of a changeable color filter or filter wheel, for example.

If in FIG. 2 the second connectors 5 of the scanner head 1 are not provided on the side of the scanner head 1 facing away from the first connector 2, this may be due to the schematic depiction of FIG. 2. Generally, the second connectors may be placed on either side of the scanner head 1, for example by means of optical waveguides running in the scanner head 1. An arrangement on the side of the scanner head 1 facing away from the connector 2 may, however, be preferred to keep the inner setup of the scanner head 1 as simple as possible.

Figure 3:
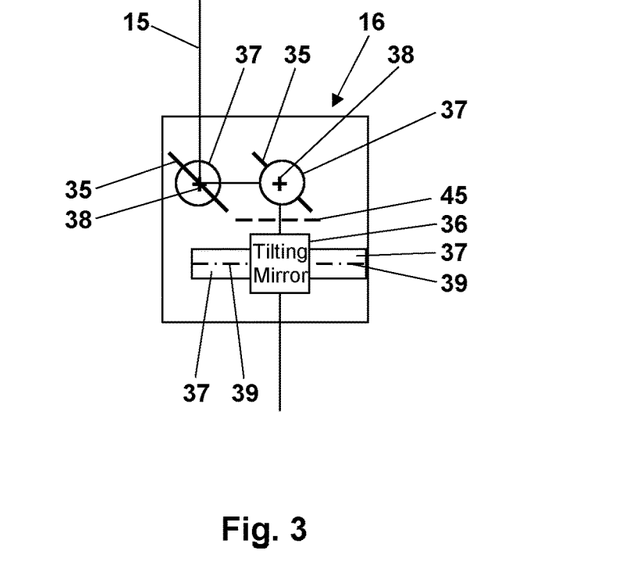
FIG. 3 shows the embodiment of a scanner of the scanner head according to the present disclosure according to FIG. 1 or FIG. 2.

FIG. 3 shows a preferred embodiment of the scanner 16 according to FIG. 1. The scanner 16 comprises two pairs of tilting mirrors 35 and 36, which may be tilted around tilting axes 38 and 39 independently of each other with drives 37. The two pairs of tilting mirrors 35 and 36 are arranged around a plane 45, onto which, according to the definition of the mount 3 according to the FIGS. 1 and 2, an image plane of the objective lens 27 of the light microscope 4 falls. Each pair of tilting mirrors 35 or 36 is provided for scanning of the sample 26 according to FIG. 2 in one scanning direction orthogonal to the optical axis of the objective lens 27. Through the use of the two tilting mirrors 35 or 36 per scanning direction, not only may the deflecting angle of the light beam 15 be set in the respective direction by the scanner 16, but also the point of passing through a pupil of the objective lens 27 of the light microscope 4 may be defined or kept fixed. This a prerequisite for reaching the desired light intensity distributions in the focus of the objective lens 27 especially with regard to the fluorescence inhibition light, which has to pass as centrally as possible through the pupil of the objective lens 27.

Figure 4:
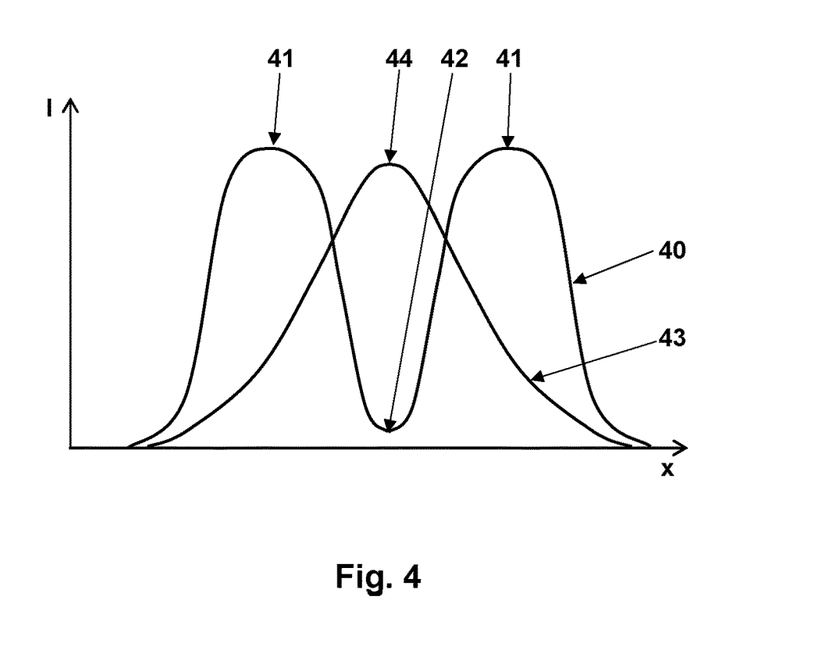
FIG. 4 shows intensity distributions of parts of the light in the focal point of the light microscope which is upgraded to a scanning fluorescence microscope with the laser scanner according to the present disclosure.

FIG. 4 shows these light intensity distributions in a cutaway through the focal point, i.e. the focal plane of the objective lens 27 according to FIG. 2. At the place where the excitation light 43 has its intensity maximum 44, the fluorescence inhibition light 40 comprises an intensity minimum 42 surrounded by intensity maxima 41. In the ideal case, the intensity minimum 42 is a zero point of the intensity distribution of the fluorescence inhibition light 40. The fluorescence light emitted by the fluorophores in the sample 22 according to FIG. 2 therefore only originates from a region around the intensity minimum 42 in which the intensity of the fluorescence inhibition light 40 is not so high that it completely inhibits the fluorescence of the fluorophores. Everywhere outside this region, the intensity of the fluorescence inhibition light 40 is above a saturation limit of the fluorescence inhibition.

Figure 5:
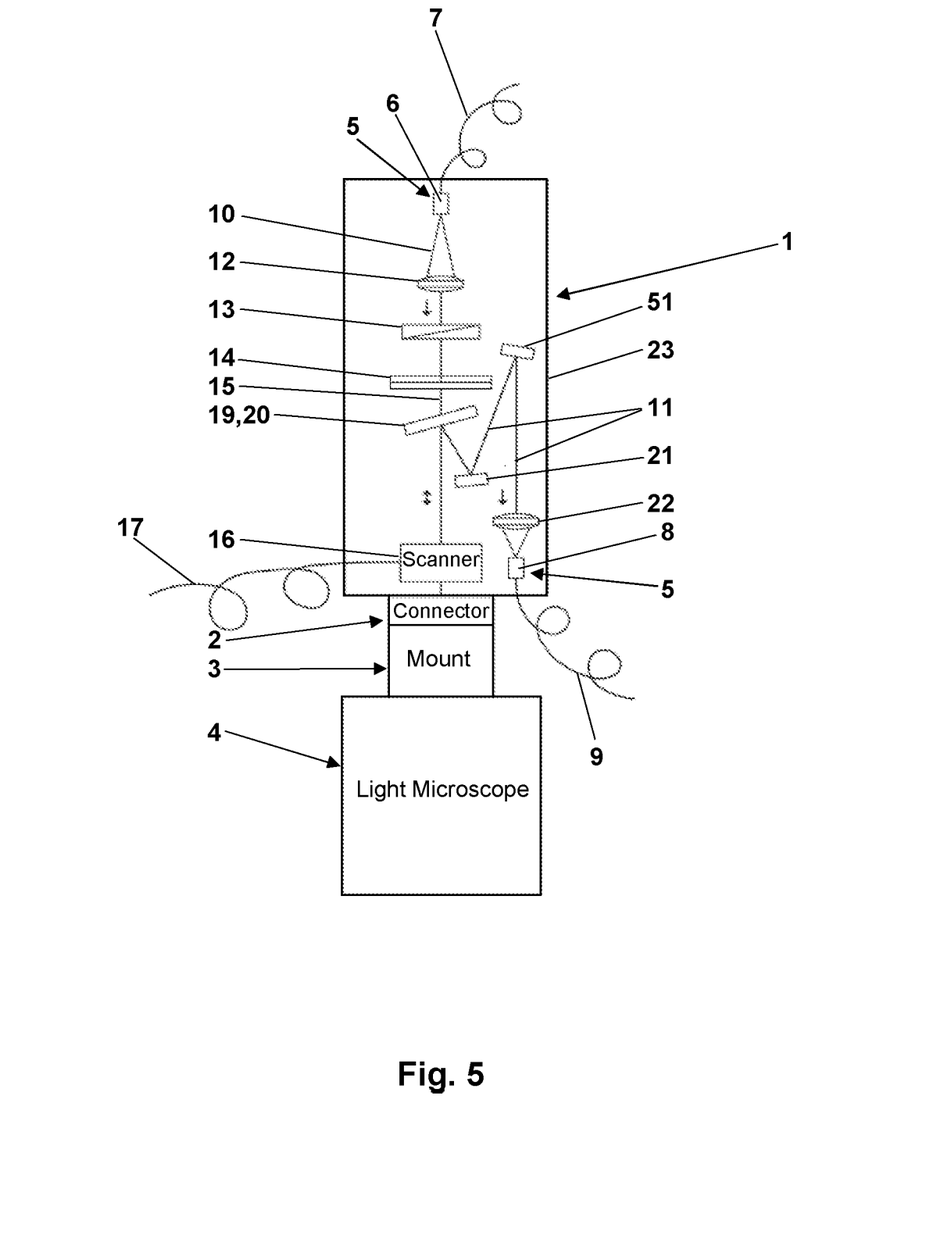
FIG. 5 schematically shows a further embodiment of the scanner head according to the present disclosure connected to a light microscope.

In the embodiment of the scanner head 1 according to FIG. 5, the optical waveguide port 8 for the fluorescence light 11 is not parallel to the optical waveguide port 6 for the light 10 from the light source, but antiparallel to it, i.e. on the same side of the scanner head 1 as the mount 3. In order to achieve this, an additional full mirror 51 is placed in the beam path of the fluorescence light 11. Furthermore, the optical waveguide ports 6 and 8 and the control cable port 18 are placed inside the housing 23, in which pass-through openings for the fiber optical waveguides 7 and 9 and the control cable 17 are provided.

Figure 6:
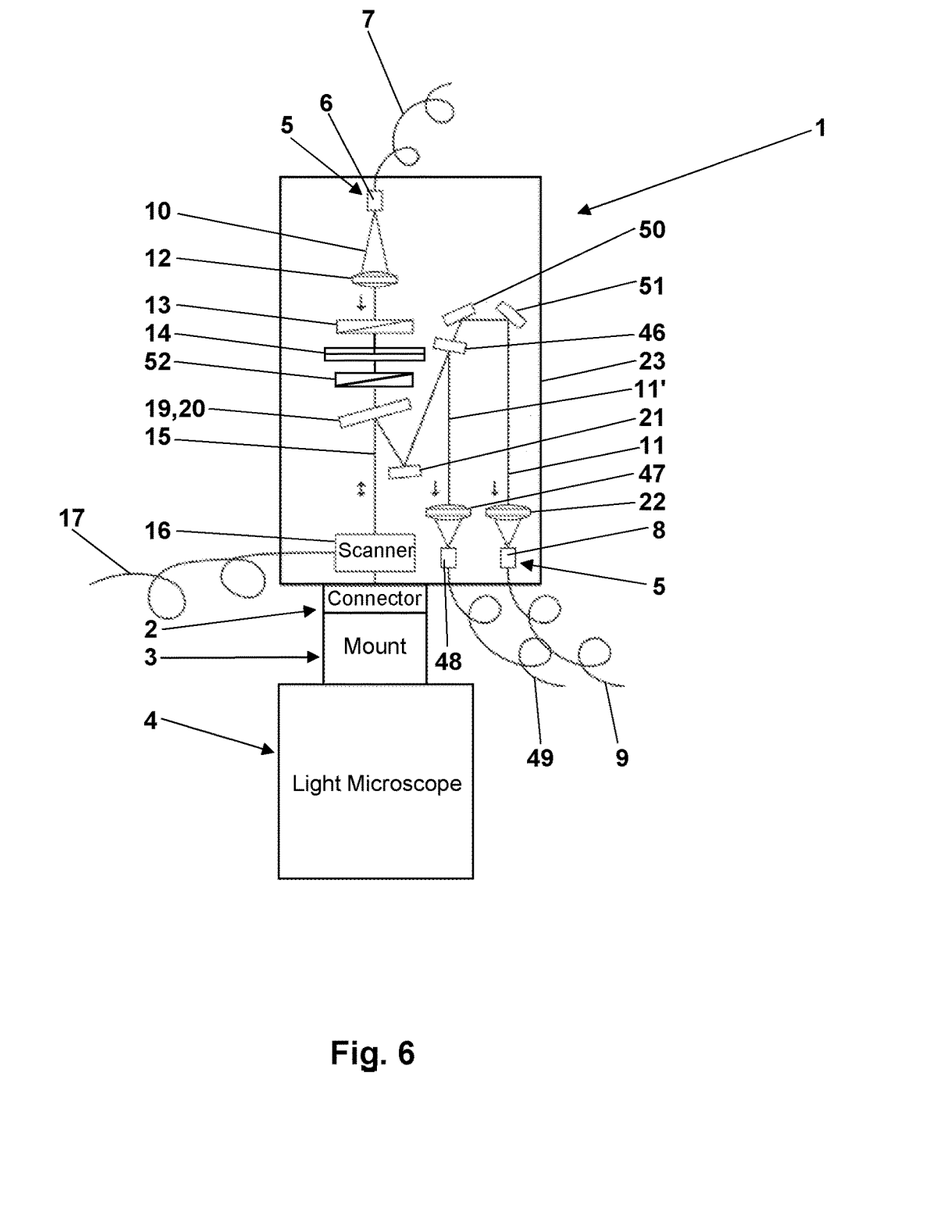
FIG. 6 schematically shows yet a further embodiment of the scanner head according to the present disclosure connected to a light microscope.

In the embodiment of the scanner head 1 according to FIG. 6, a birefringent plate 52 is placed between the phase plate 14 and the deflector 20. In a first, standard orientation, the birefringent plate 52 is oriented with its fast axis parallel to the light beam 15. Thus, the circularly polarized light beam 15 passes through the birefringent plate 52 unaffected. However, the birefringent plate 52 may be tilted if required to introduce a distortion in the polarization of the light beam 15. The tilting of the birefringent plate 52 may, for example be adjusted or set by turning adjustment screws which are not depicted here. The tilting of the birefringent plate 52 and therefore the distortion in the polarization of the light beam 15 may be chosen specifically to offset or pre-compensate any distortion in the polarization of the light beam 15 caused by downstream optical elements, especially the light microscope 4. In this way the birefringent plate 52 can be used to distort the polarization of the light beam 15 intentionally in just such a way that imperfections of the downstream optical elements are anticipated so that the light beam 15 after passing the imperfect optical elements is circularly polarized again (instead of becoming e. g. elliptically polarized due to the imperfections).

In a further variation to the embodiments shown in FIGS. 1 and 5, a part 11' of the fluorescence light is deflected from the beam path between the dichroic mirror 19 and the optical waveguide port 8 with the aid of a further dichroic mirror 46 towards an additional coupling lens 47, which injects the part 11' of the fluorescence light into a multi-mode fiber optical waveguide 49. For the additional multi-mode fiber optical waveguide 49, a further optical waveguide port 48 is provided. The rest of the fluorescence light 11 is led to the further coupling lens 22 via an additional full mirror 50 and the full mirror 51. With regard to their reflection and transmission bands, the dichroic mirrors 19 and 46 are coordinated with each other in such a way that the fluorescence light 11 of different wavelengths from different fluorophores in the respective sample is injected into the two multi-mode fiber optical waveguides 9 and 49 separately and therefore may be guided towards separate detector units of the detector for the fluorescence light.

Many variations and modifications may be made to the preferred embodiments of the invention without departing substantially from the spirit and principles of the present disclosure. All such modifications and variations are intended to be included herein within the scope of the present disclosure, as defined by the following claims.

We claim:

1. A scanner head for high-resolution scanning fluorescence microscopy comprising
 a housing,
 a first connector arranged on or in the housing and configured to connect the scanner head to a light microscope,
 second connectors arranged on or in the housing and configured to connect the scanner head to an external light source and an external fluorescence light detector via fiber optical waveguides,
 a beam shaper encased in the housing and arranged between the second connectors and the first connector and configured to shape light from the external light source into a light beam and
 tilting mirrors encased in the housing and arranged between the beam shaper and the first connector and configured to deflect the light beam by different deflection angles in such a way that a sample into which the light beam is focused by the light microscope is scanned in two different directions by the light beam, while fluorescence light from the sample is guided back to the second connectors,
 wherein the first connector is configured to connect the scanner head to a mount of the light microscope, the mount having a first defined relative position with regard to an intermediate image of the sample imaged by the light microscope so that the intermediate image has a second defined relative position with regard to the tilting mirrors,
 wherein the second connectors comprise a first optical waveguide port configured to receive the light from the light source and a separate second optical waveguide port configured to output the fluorescence light to the detector,
 wherein a deflector is arranged between the tilting mirrors and the first optical waveguide port and configured to deflect the fluorescence light to the second optical waveguide port,
 wherein the beam shaper is configured to shape a first part of the light from the light source into a first light intensity distribution in the focus of the light microscope comprising an intensity minimum surrounded by intensity maxima and a second part of the light from the light source into a second light intensity distribution in the focus of the light microscope comprising an intensity maximum at the location of the intensity minimum of the first light intensity distribution, and wherein the tilting mirrors include four tilting mirrors each having a drive and a tilting axis wherein the four drives are configured to be controlled independently of each other in order to tilt the four tilting mirrors around their respective tilting axes.

2. A scanner head according to claim 1, wherein the first connector is configured to connect the scanner head to a camera mount or another mount of the light microscope which is at least one of fully corrected and standardized.

3. A scanner head according to claim 1, wherein the first connector is configured to support the scanner head in a fixed position at the mount of the light microscope.

4. A scanner head according to claim 1, wherein the tilting mirrors are arranged around a plane onto which the intermediate image falls.

5. A scanner head according to claim 1, wherein the first optical waveguide port is positioned on a side of the scanner head opposite of the first connector, whereas the second optical waveguide port is positioned either on the side of the scanner head opposite the first connector or on the same side of the scanner head as the first connector.

6. A scanner head according to claim 1, wherein the beam shaper comprises a beam shaping arrangement with a common light path for the first and second parts of the light from the light source, which shapes the first part of the light from the light source in such a way that it comprises the intensity minimum surrounded by the intensity maxima in the focus of the light microscope and which shapes the second part of the light from the light source in such a way that it comprises the intensity maximum at the location of the intensity minimum of the first part of the light in the focus of the light microscope.

7. A scanner head according to claim 1, wherein a birefringent plate is placed between the beam shaper and the deflector, wherein the birefringent plate, in a standard orientation, is oriented with its fast axis parallel to the light beam and wherein the birefringent plate is configured to be tilted.

8. A scanner head according to claim 1 that has maximum dimensions in a direction of an optical axis of the mount and perpendicular to the optical axis of not more than 25 cm and a mass of no more than 1.5 kg.

9. A scanner head according to claim 1, wherein a control cable port for a control cable to connect the drives of the tilting mirrors to an external controller is arranged on or in the housing.

10. A device for upgrading a light microscope to a high-resolution scanning fluorescence microscope with
- a base unit comprising a light source providing light, a detector configured to detect fluorescence light and a controller,
- a first optical waveguide, a first end of the first optical waveguide being connected to the light source,
- a second optical waveguide, a first end of the first optical waveguide being connected to the detector,
- a control cable, a first end of the control cable being connected to the controller, and
- a scanner head separated from the base unit and comprising
  - a housing,
  - a first connector arranged on or in the housing and configured to connect the scanner head to a light microscope,
  - a first optical waveguide port arranged on or in the housing, to which a second end of the first optical waveguide is connected, and a separate second optical waveguide port arranged on or in the housing, to which a second end of the second optical waveguide is connected,
  - a beam shaper encased in the housing and arranged between the first optical waveguide port and the first connector and configured to shape the light provided by the light source into a light beam, and
  - tilting mirrors encased in the housing and arranged between the beam shaper and the first connector and deflecting the light beam by different deflection angles in such a way that a sample into which the light beam is focused by the light microscope is scanned in two different directions by the light beam, while fluorescence light from the sample is guided back to the second optical waveguide port,
  - wherein the first connector is configured to connect the scanner head to a mount of the light microscope, the mount having a first defined relative position with regard to an intermediate image of the sample imaged by the light microscope so that the intermediate image has a second defined relative position with regard to the tilting mirrors,
  - wherein a deflector is arranged between the tilting mirrors and the first optical waveguide port and configured to deflect the fluorescence light to the second optical waveguide port,
  - wherein the beam shaper is configured to shape a first part of the light from the light source into a first light intensity distribution in the focus of the light microscope comprising an intensity minimum surrounded by intensity maxima and a second part of the light from the light source into a second light intensity distribution in the focus of the light microscope comprising an intensity maximum at the location of the intensity minimum of the first light intensity distribution, and
  - wherein the tilting mirrors include four tilting mirrors each having a drive and a tilting axis, wherein the four drives are connected to a second end of the control cable and controlled by the controller independently of each other in order to tilt the four tilting mirrors around their respective tilting axes.

11. A device according to claim 10, wherein the first optical waveguide comprises a single-mode fiber optical waveguide and the second optical waveguide comprises at least one multi-mode fiber optical waveguide.

12. A device according to claim 10, wherein the base unit comprises at least one of a supply port for feeding a supply low voltage and a communication port for connecting to a control computer.

13. A device according to claim 10, wherein the light source comprises at least two lasers, which emit at different wavelengths.

14. A device according to claim 10, further comprising a sample holder which is height-adjustable by controlling an actuator, wherein the actuator is connected to a further controller in the base unit by a further control cable.

15. A high-resolution scanning fluorescence microscope comprising
- a light microscope comprising a mount having a first defined relative position with regard to an intermediate image of a sample imaged by the light microscope,
- a light source providing light,
- a fluorescence light detector configured to detect fluorescence light, a first optical waveguide, a first end of the first optical waveguide being connected to the light source, a second optical waveguide, a first end of the second optical waveguide being connected to the detector, a controller, a control cable, a first end of the control cable being connected to the controller, and a scanner head separated from the light source and the fluorescence light detector, and comprising a housing, a first connector arranged on or in the housing and connecting the scanner head to the mount of the light microscope, a first optical waveguide port to which a second end of the first optical waveguide is connected, and a separate second optical waveguide port to which the second end of the second optical waveguide is connected, a beam shaper encased in the housing and arranged between the second connectors and the first connector that shapes a first part of the light from the light source into a first light intensity distribution in the focus of the light microscope comprising an intensity minimum surrounded by intensity maxima and a second part of the light from the light source into a second light intensity distribution in the focus of the light microscope comprising an intensity maximum at the location of the intensity minimum of the first light intensity distribution, tilting mirrors encased in the housing and arranged between the beam shaper and the first connector that deflect the light shaped by the beam shaper by different deflection angles in such a way that the sample, into which the light beam is focused by the light microscope, is scanned in two different directions by the light beam, while fluorescence light from the sample is guided back to the second connectors, the tilting mirrors including four tilting mirrors each having a drive and a tilting axis, the drives being connected to a second end of the control cable, the controller controlling the four drives of the tilting mirrors independently of each other in order to tilt the four tilting mirrors around their respective tilting axes, and the intermediate image having a second defined relative position with regard to the tilting mirrors, wherein a deflector is arranged between the tilting mirrors and the first optical waveguide port that deflects the fluorescence light coming from the sample to the second optical waveguide port.

16. A high-resolution scanning fluorescence microscope according to claim 15, wherein the tilting mirrors are arranged around a plane onto which the intermediate image falls.

17. A high-resolution scanning fluorescence microscope according to claim 15, wherein the first optical waveguide comprises a single-mode fiber optical waveguide and the second optical waveguide comprises at least one multi-mode fiber optical waveguide.

18. A high-resolution scanning fluorescence microscope according to claim 15, wherein the mount of the light microscope is a camera mount or another mount which is at least one of fully corrected and standardized.

19. A high-resolution scanning fluorescence microscope according to claim 15, wherein the light source comprises at least two lasers, which emit at different wavelengths.

20. A high-resolution scanning fluorescence microscope according to claim 15, further comprising a sample holder which is height-adjustable by controlling an actuator, wherein the actuator is connected to a further controller by a further control cable.

* * * * *